(12) United States Patent
Rizzardo et al.

(10) Patent No.: US 6,512,081 B1
(45) Date of Patent: Jan. 28, 2003

(54) SYNTHESIS OF DITHIOESTER CHAIN TRANSFER AGENTS AND USE OF BIS (THIOACYL) DISULFIDES OR DITHIOESTERS AS CHAIN TRANSFER AGENTS

(75) Inventors: Enzio Rizzardo, Wheelers Hill (AU); San Hoa Thang, Clayton South (AU); Graeme Moad, Kallista (AU)

(73) Assignees: E.I. DuPont Nemours and Company, Wilmington, DE (US); Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/743,802
(22) PCT Filed: Jul. 20, 1998
(86) PCT No.: PCT/AU98/00569
§ 371 (c)(1),
(2), (4) Date: Jan. 22, 2001
(87) PCT Pub. No.: WO99/05099
PCT Pub. Date: Feb. 4, 1999

Related U.S. Application Data

(60) Provisional application No. 60/053,208, filed on Jul. 21, 1997.

(51) Int. Cl.[7] .............................................. C08G 75/26
(52) U.S. Cl. ..................... 528/340; 528/373; 525/212; 525/222; 525/535
(58) Field of Search ................................ 528/390, 373; 525/212, 222, 535

(56) References Cited

U.S. PATENT DOCUMENTS 5,342,901 A    8/1994    Kogure et al. ........... 525/330.5

FOREIGN PATENT DOCUMENTS

| EP | 365792 A | 5/1909 |
| WO | WO 92/13902 A | 8/1992 |
| WO | WO 98/01478 A | 1/1998 |

*Primary Examiner*—Duc Truong
(74) *Attorney, Agent, or Firm*—Bacon & Thomas

(57) ABSTRACT

This invention relates to the synthesis of dithiocarboxylic acid esters by reaction of bis(thioacyl) disulphides, thioacetals or vinylidane bis(thioether) with free-radicals (optionally in the presence of monomers). The invention also relates to processes for the synthesis of polymers utilising these dithioesters as polymerisation regulators (chain transfer agents) or to the use of bis(thioacyl) disulphides to generate dithioester chain transfer agents in situ.

25 Claims, No Drawings

SYNTHESIS OF DITHIOESTER CHAIN TRANSFER AGENTS AND USE OF BIS (THIOACYL) DISULFIDES OR DITHIOESTERS AS CHAIN TRANSFER AGENTS

This application claims benefit under 35 U.S.C. 119(e) of U.S. provisional application Ser. No. 60/053,208, filed Jul. 21, 1997.

BACKGROUND OF THE INVENTION

This invention relates to the synthesis of dithioesters which can be utilized in a free radical polymerization process with characteristics of a living polymerization. The diothioesters may be monomeric, oligomeric or polymeric. The invention also relates to processes for the synthesis of polymers utilising these dithioesters.

There is increasing interest in methods for producing a variety of polymers with control of the major variables affecting polymer properties. Living polymerizations provide the maximum degree of control for the synthesis of polymers with predictable well defined structures. The characteristics of a living polymerization are discussed by Quirk and Lee (*Polymer International* 27, 359 (1992)) who give the following experimentally observable criteria:

"1. Polymerization proceeds until all of the monomer has been consumed. Further addition of monomer results in continued polymerization.
2. The number average molecular weight (or the number average degree of polymerization) is a linear function of conversion.
3. The number of polymer molecules (and active centers) is a constant which is sensibly independent of conversion.
4. The molecular weight can be controlled by the stoichiometry of the reaction.
5. Narrow molecular weight distribution polymers are produced.
6. Block copolymers can be prepared by sequential monomer addition.
7. Chain end-functionalised polymers can be prepared in quantitative yield."

Thus living polymerization processes can be used to produce polymers of narrow molecular weight distribution containing one or more monomer sequences whose length and composition are controlled by the stoichiometry of the reaction and the degree of conversion. Homopolymers, random copolymers and/or block polymers may be produced with a high degree of control and with low polydispersity.

Syntheses of certain polymers with xanthate or dithiocarbamate end groups from the corresponding disulfides have been described in the literature (see for example, Moad and Solomon "The Chemistry of Free Radical Polymerization", Pergamon, London, 1995, pp 337–339; Nair and Clouet *J. Macromol. Sci., Rev. Macromol. Chem. Phys.*, 1991, C31, 311). Processes have also been described that use these compounds to prepare block copolymers. However, the processes using these compounds are unsuccessful in producing low polydispersity polymers and do not meet many of the criteria for living polymerization as defined above.

WO 98/01478, the entire contents of which is incorporated herein by reference, describes the use of chain transfer agents (CTAs) of the following structure:

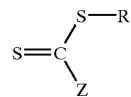

in free radical polymerisation processes with living characteristics to provide polymers of controlled molecular weight and low polydispersity.

It has now been found that CTAs of this structure can be prepared in a convenient manner from a single disulphide reagent, or generated in situ in the polymerisation vessel.

SUMMARY OF THE INVENTION

Accordingly the present invention provides a process for the synthesis of dithioesters formula I:

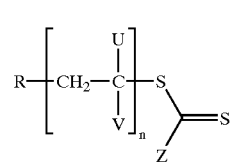

where R is derived from a free radical R. and is selected from the group consisting of optionally substituted alkyl; optionally substituted, saturated, unsaturated or aromatic carbocyclic rings; optionally substituted, saturated, unsaturated or aromatic heterocyclic rings; optionally substituted alkylthio, optionally substituted arylthio; optionally substituted alkoxy; optionally substituted dialkylamino; organometallic species; and polymer chains; R. is a free radical leaving group;

U is independently selected from the group consisting of hydrogen; halogen; and $C_{1-4}$ alkyl optionally substituted with one or more substituents independently selected from the group consisting of hydroxy, carboxy, acyloxy, OR", $O_2CR"$ and $CO_2R"$;

V is independently selected from the group consisting of hydrogen, halogen, R", $CO_2H$, $CO_2R"$, COR", CN, $CONH_2$, CONHR", $CONR_2"$, $O_2CR"$ and OR";

Z is selected from the group consisting of hydrogen, chlorine, optionally substituted alkyl, optionally substituted aryl, optionally substituted alkylthio, optionally substituted alkoxycarbonyl, $—CO_2R"$, $—CO_2H$, $—O_2CR"$, $—CONR_2"$, cyano, $—[P(=O)(OR"_2)]$, and $—[P(=O)R"_2]$;

R" is independently selected from the group consisting of optionally substituted $C_{1-18}$ alkyl, optionally substituted $C_{2-18}$ alkenyl, optionally substituted aryl, optionally substituted heterocyclyl, optionally substituted aralkyl, optionally substituted alkaryl, wherein said optional substituents are selected from the group consisting of epoxy, alkoxycarbonyl, aryloxycarbonyl, isocyanato, cyano, silyl, halo and dialkylamino;

and n is 0 or a positive integer, which process includes contacting a disulphide of the Formula II

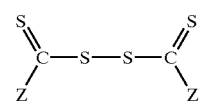

with
(i) in the case of n=0, a free radical of the formula R., or (ii) in the case of n>0, a free radical of the formula R. and at least one monomer of the formula III

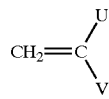

R may be selected from any organic group which is derived from the corresponding radical, R., which radical can act as a free radical leaving group. Preferably the radical, R., is capable of initiating free radical polymerisation. Examples of suitable radicals include carbon centred, sulphur centred, and in some circumstances, oxygen or nitrogen centred radicals. Where R is a polymer chain it may be produced by means of free radical polymerisation, or any other means, such as condensation polymerisation.

The term "free radical leaving group" as used herein refers to a group which departs as a free radical during a substitution or displacement reaction.

R may also be derived from a dithioester of formula I generated in situ, or may be derived from an initiating radical or a propagating radical.

Preferably Z is selected to give the C=S bond a high reactivity towards radical addition while not slowing the subsequent rate of fragmentation in the presence of the monomer to the extent that there is an unacceptable retardation of polymerization.

When conducted in the presence of a monomer of formula III the process according to the invention is useful for the preparation of a wide variety of polymer types, including homopolymers, copolymers and block copolymers. Homopolymers may be prepared by using a single monomer of formula III, while copolymers may be prepared by using two or more monomers. Block copolymers may be prepared by contacting a first monomer of formula III with the disulphide of formula II and free radical of formula R. to produce an intermediate homopolymer of formula I, and then contacting the homopolymer with a second monomer of formula III and a free radical of formula R. Further blocks can be add in like manner.

The invention also relates to the used of a disulphide of formula II to provide chain transfer in a free radical polymerization process, and to the use of the disulphide in the preparation of a chain transfer agent of formula I for use in a free radical polymerisation process.

DETAIL OF THE INVENTION

Free radical polymerizations in the presence of chain transfer agents (CTAs) represented by the following structure has been described in Le et al. Int. Patent Appl. WO 98/01478.

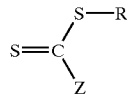

Such polymerizations possess the characteristics of a living polymerization in that they are capable of producing polymers of pre-determined molecular weight with narrow molecular weight distribution (low polydispersity), and, by successively adding different monomers, can be used to make block polymers. The process can also be used to produce polymers of more complex architecture, including variously branched homo- and copolymers.

It has now been found that certain materials which are not CTAs of the above structure may nonetheless be utilized as precursor materials to said CTAs and with suitable choice of reaction conditions can be used in a 'one-pot' synthesis of CTA and narrow polydispersity polymer.

In particular it has now been found that compounds of Formula II react with free radicals produced from a radical source (e.g. an azo compound) to form CTAs of Formula I in moderate to high yields.

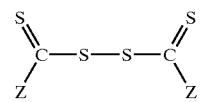

Formula II

The reaction may optionally be carried out in the presence of a monomer. The initial product may, in this case, be an oligomeric CTA of Formula I.

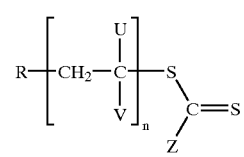

Formula I

When the compound of Formula II is largely consumed polymerization can proceed according to the process disclosed in WO98/01478. It has been found that the overall procedure can be used to synthesise narrow polydispersity and block polymers without the need for product isolation. The process may also be adapted to the synthesis of polymers of more complex architecture through appropriate choice of compound of Formula II and monomers.

The source of free radicals should chosen such that (i) there is a minimum level of initiator derived by-products.

(ii) the derived group R conveys appropriate reactivity to the product CTA of Formula I.

(iii) the radical R. is capable of adding to the desired monomer(s) (so as initiate subsequent polymerization steps).

The requirements for R groups in compounds of Formula I have been described in detail by Le et al. Int. Patent Appl. WO 98/01478.

As used herein the term "dithioester" refers to a compound, which may be monomeric, oligomeric of polymeric having a —(C=S)S— moiety.

Unless specified otherwise the term "alkyl" used either alone or in compound words such as "alkenyloxyalkyl" and "alkylthio" denotes straight chain or branched alkyl, preferably $C_{1-20}$alkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2-ethylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1,2-pentylheptyl and the like.

The term "alkoxy" denotes straight chain or branched alkoxy, preferably $C_{1-20}$ alkoxy. Examples of alkoxy include methoxy, ethoxy, n-propoxy, isopropoxy and the different butoxy isomers.

The term "alkenyl" denotes groups formed from straight chain or branched alkenes including ethylenically mono-, di- or poly-unsaturated alkyl groups as previously defined, preferably $C_{2-20}$ alkenyl. Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1-4,pentadienyl, 1,3-hexadienyl and 1,4-hexadienyl The term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl, or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

Saturated, unsaturated or aromatic carbocyclic or heterocyclic rings may contain from 3 to 20 carbon atoms.

The terms "aromatic carbocyclic ring" and "aromatic heterocyclic ring" as used herein refer to aromatic and pseudoaromatic rings which may be carbocyclic or heterocyclic, and may be mono- or polycyclic ring systems. In the case of heterocyclic rings, there will be one or more heteroatoms selected from N, S, O and P. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, pyrene, isobenzofuran, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted. The term "aromatic ring compound(s)" includes molecules, and macromolecules, such as polymers, copolymers and dendrimers which include or consist of one or more aromatic or pseudoaromatic rings. The term "pseudoaromatic" refers to a ring system which is not strictly aromatic, but which is stabilized by means of delocalization of π electrons and behaves in a similar manner to aromatic rings. Examples of pseudoaromatic rings include but are not limited to furan, thiophene, pyrrole and the like.

The terms "saturated carbocyclic ring" and "saturated heterocyclic ring" as used herein refer to carbocyclic and heterocyclic rings, which may be mono or polycyclic ring systems, and which are fully saturated. In the case of heterocyclic rings, there will be one or more heteroatoms selected from N, S, O and P. Examples of suitable rings include, but are not limited to, cyclobutane, cyclopentane, cyclohexane, cyclopentane, imidazolidene, pyrazolidene and the like.

The terms "unsaturated carbocyclic ring" and "unsaturated heterocyclic ring" as used herein refer to carbocyclic and heterocyclic rings, which may be mono or polycyclic, which have one or more degrees of unsaturation. In the case of heterocyclic rings, there will be one or more heteroatoms selected from N, S, O and P. Examples of suitable rings include cyclopentene, cyclohexene, imidazoline and pyrazoline.

Initiating radicals are free radicals that are derived from the initiator or other species which add monomer to produce propagating radicals. Propagating radicals are radical species that have added one or more monomer units and are capable of adding further monomer units.

The term "polymer" as used herein includes oligomers and in the case of dithioesters of formula I refers to those in which n>1. The upper limit of a "n" will be defined by the particular conditions and reactants employed, as well as the characteristics of the growing polymer chain.

All of the benefits which derive from the use of radical polymerization can now be realized in synthesis of low polydispersity homo- and copolymers. The ability to synthesize block, graft, star, gradient and end-functional polymers further extends the value of the process as does compatibility with protic monomers and solvents.

The source of initiating radicals can be any suitable method of generating free radicals such as the thermally induced homolytic scission of a suitable compound(s) (thermal initiators such as peroxides, peroxyesters, or azo compounds), the spontaneous generation from monomer (e.g., styrene), redox initiating systems, photochemical initiating systems or high energy radiation such as electron beam, X- or gamma-radiation. The initiating system is chosen such that under the reaction conditions there is no substantial adverse interaction of the initiator or the initiating radicals with the transfer agent under the conditions of the experiment. The initiator should also have the requisite solubility in the reaction medium or monomer mixture.

Suitable sources of free radicals for the process carried out in the absence of monomer are those which generate carbon-centred radicals. These include azo compounds and certain peroxides such as:

2,2'-azobis(isobutyronitrile), 2,2'-azobis(2-cyano-2-butane), dimethyl 2,2'-azobis(methyl isobutyrate), 4,4'-azobis(4-cyanopentanoic acid), 4,4'-azobis(4-cyanopentan-1-ol), 1,1'-azobis(cyclohexanecarbonitrile), 2-(t-butylazo)-2-cyanopropane, 2,2'-azobis[2-methyl-(N)-(1,1)-bis(hydroxymethyl)-2-hydroxyethyl] propionamide, 2,2'-azobis[2-methyl-N-hydroxyethyl)]-propionamide, 2,2'-azobis(N,N'-dimethyleneisobutyramidine) dihydrochloride, 2,2'-azobis(2-amidinopropane) dihydrochloride, 2,2'-azobis(N,N'-dimethyleneisobutyramine), 2,2'-azobis(2-methyl-N-[1,1-bis(hydroxymethyl)-2-hydroxyethyl] propionamide), 2,2'-azobis(2-methyl-N-[1,1-bis(hydroxymethyl)ethyl]propionamide), 2,2'-azobis[2-methyl-N-hydroxyethyl)propionamide], 2,2'-azobis(isobutyramide)dihydrate, 2,2'-azobis(2,2,4-trimethylpentane), 2,2'-azobis(2-methylpropane), dilauroyl peroxide, tertiary amyl peroxides and tertiary amyl peroxydicarbonates.

For reactions carried out in the presence of monomer where the properties of R. are determined by the nature of the propagating radical formed by addition to monomer a wider range of free radical sources may be used. These include sources of oxygen centred radicals such as the following initiators:

t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, potassium peroxydisulfate, ammonium peroxydisulfate, di-t-butyl hyponitrite, dicumyl hyponitrite.

Photochemical initiator systems are chosen to have the requisite solubility in the reaction medium or monomer mixture and have an appropriate quantum yield for radical production under the conditions of the polymerization. Examples include benzoin derivatives, benzophenone, acylphosphine oxides, and photo-redox systems.

Redox initiator systems are chosen to have the requisite solubility in the reaction medium or monomer mixture and have an appropriate rate of radical production under the conditions of the polymerization, there initiating systems can include combinations of the following oxidants and reductants:

oxidants: potassium peroxydisulfate, hydrogen peroxide, t-butyl hydroperoxide.

reductants: iron (II), titanium (III), potassium thiosulfite, potassium bisulfite.

Other suitable initiating systems are described in recent texts. See, for example, Moad and Solomon "The Chemistry of Free radical Polymerization", Pergamon, London, 1995, pp53–95.

Compounds suitable as monomers or comonomers include the following:

methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethylacrylamide, N-n-butylmethylacrylamide, N-methylolmethylacrylamide, N-ethylolmethylacrylamide, N-tert-butylacrylamide, N-n-butylacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), n-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethyl-silylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, isoprene, chloroprene, ethylene and propylene.

Particularly preferred monomers include styrenic and methacrylate monomers.

Unless otherwise specified the term "optionally substituted" as used herein means that the compound, moiety or atom may be substituted with one or more substituents selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, isocyano, cyano, formyl, carboxyl, dialkylamino, acyl, alkenylacyl, alkynylacyl, arylacyl, acyloxy, alkylsulphonyloxy, arylsulphenyloxy, heterocyclyl, heterocycloxy, haloheterocyclyl, alkylsulphenyl, arylsulphenyl, carboalkoxy, carboaryloxy mercapto, alkylthio, benzylthio, acylthio, sulphonamido, sulfanyl, sulfo and phosphorus-containing groups, alkoxysilyl, silyl, alkylsilyl, alkylalkoxysilyl, phenoxysilyl, alkylphenoxysilyl, alkoxyphenoxy silyl and arylphenoxy silyl.

These substituents do not take part in the polymerization reactions but form part of the terminal groups of the polymer chains and may be capable of subsequent chemical reaction.

The low polydispersity polymer containing any such reactive group is thereby able to undergo further chemical transformation, such as being joined with another polymer chain. Suitable reactive substituents include: epoxy, hydroxy, alkoxy, acyl, acyloxy, carboxy (and salts), sulfonic acid (and salts), alkylcarbonyloxy, isocyanato, cyano, silyl, halo, and dialkylamino. Alternatively, the substituents may be non-reactive such as alkoxy, alkyl or aryl. Reactive groups should be chosen such that there is no adverse reaction with the CTA under the conditions of the experiment. For example, groups such as primary or secondary amino under some conditions may react with dithioesters to give thioamides thus destroying the CTA.

The process of this invention offers a route of compounds of Formula I that may be otherwise difficult to prepare.

One application is the synthesis of functional dithioesters from an azo compound containing the appropriate functionality as illustrated in the following Scheme.

Scheme 1

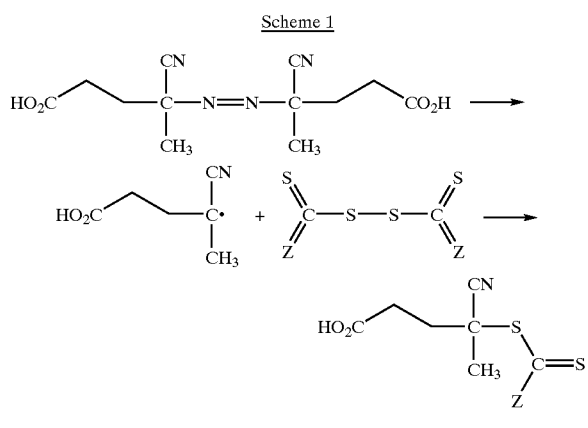

When conducted in the presence of monomers the process also offers a route to narrow polydispersity and block polymers and may be adapted to produce polymers of more complex architecture.

Whilst not wishing to be limited to any particular mechanism, it is believed that the mechanism of the process is as summarized in Scheme 2 below. Radicals (R.) are formed from a source of free radicals. These react with the compound 2 to form a compound 1 and a thiocarbonylthio radical 3.

Scheme 2

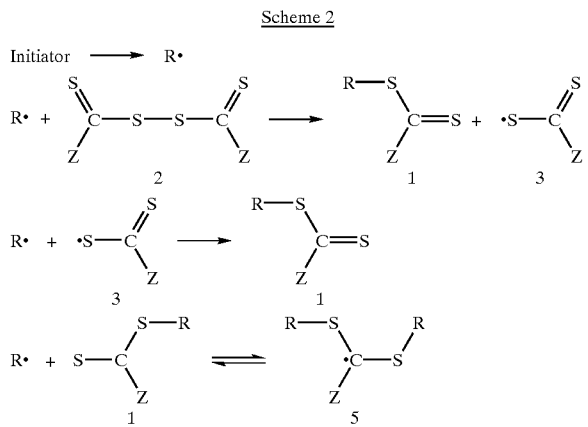

The thiocarbonylthio radical 3 is a poor initiator of polymerization and under the reaction conditions most likely consumed by coupling with another free radical. This radical may be a thiocarbonylthio radical to reform compound 2 or an initiator derived radical (R.) to form further compound 1.

The main side reactions occurring under the reaction conditions are most likely the self reaction of species R. and other reactions involving the source of free radicals.

For reactions carried out in the presence of a monomer the radical R. may undertake one or more monomer additions before reaction with 1 or 3. In this case the product will be of formula I with n>0.

It has also been found that other compounds and processes which generate dithioester compounds of Formula I may be used in similar fashion and thus also form part of this invention. Compounds of this type are represented by formulae V and VI.

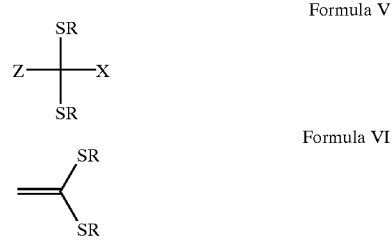

Formula V

Formula VI

Accordingly in another aspect of the present invention there is provided a process for the synthesis of a dithioester of Formula I from a compound of Formula V:

Formula V $$Z-\underset{\underset{S-R}{|}}{\overset{\overset{S-R}{|}}{C}}-X$$

where Z is as defined above,

X is hydrogen, halogen, acyl, aryl or phosphine oxide, and each R is the same or different and is selected from the group consisting of optionally substituted alkyl; optionally substituted, saturated, unsaturated or aromatic carbocyclic rings; optionally substituted, saturated, unsaturated or aromatic heterocyclic rings; optionally substituted alkylthio, optionally substituted arylthio; optionally substituted alkoxy; optionally substituted dialkylamino; organometallic species; and polymer chains; and where the corresponding radical, R., is a free radical leaving group; by A) in the case of n=0, (i) where X is not hydrogen, homolytic cleavage of the C—X bond of a compound of formula V and subsequent elimination of R., (ii) where X is hydrogen, contacting a compound of formula V with a hydrogen abstracting radical followed by elimination of R., or (iii) contacting a compound of formula V with a Lewis acid followed by elimination of R., or B) in the case of n>0, performing any of (i), (ii) or (iii) in the presence of a monomer of formula III as described above.

The homolytic cleavage may be achieved by, for example, thermal or photochemical means.

As shown below, homolytic cleavage of the C—X bond of 5 will generate radical 7 which can fragment to give a compound of 1.

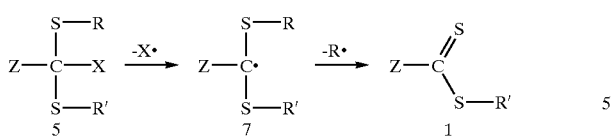

Similarly hydrogen atom abstraction from compound 8 will generate radical 7.

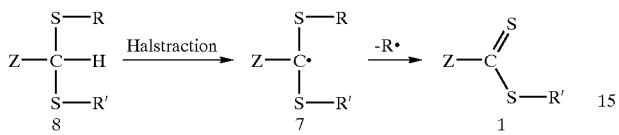

Examples of compound of Formula V are thioacetals of benzoin and related species. These compounds undergo photochemical homolytic scission.

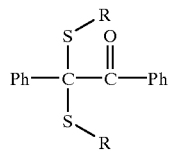

In yet another aspect there is provided a process for the synthesis of a dithioester of formula I as defined in claim 1 including contacting a compound of formula VI Formula VI

where each R is the same or different and is selected from the group consisting of optionally substituted alkyl; optionally substituted, saturated, unsaturated or aromatic carbocyclic rings; optionally substituted, saturated, unsaturated or aromatic heterocyclic rings; optionally substituted alkylthio, optionally substituted arylthio; optionally substituted alkoxy; optionally substituted dialkylamino; organometallic species; and polymer chains; and where the corresponding radical, R., is a free radical leaving group;

with (i) in the case of n=0, a free radical of formula R., or (ii) in the case of n>0, a free radical of formula R. and a monomer of Formula III.

As shown below free radical addition to compound 6 will generate an adduct 9 which can fragment to give a compound 10 (Formula I where Z=R"CH$_2$—)

R'.+

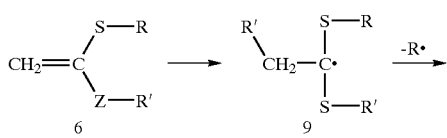

In these examples both of the groups R and R' must be a free radical leaving groups.

Benefits of the process according to the present invention including the following:

a) low polydispersity polymers can be synthesised.

b) molecular weights increase in a predictable and linear manner with conversion which is controlled by stoichiometry.

c) the process can be used to provide a variety of low polydispersity polymers.

d) the process is compatible with a wide range of monomers and reaction conditions.

e) dithioesters of complex structures may be readily synthesised.

A detailed discussion of the benefits of low polydispersity and the other advantages referred to above is provided in WO 98/01478, including a description of how reactants and conditions can be adjusted to provide desired results.

EXAMPLES

General Experimental Conditions

Monomers were purified (to remove inhibitors) and flash distilled immediately prior to use. Degassing was accomplished by repeated freeze-evacuate-thaw cycles. Once degassing was complete ampoules were flame sealed under vacuum and completely submerged in an oil bath at the specified temperature for the specified times. The percentage conversions were calculated gravimetrically.

The structures of polymers and block copolymers have been verified by application of appropriate chromatographic and spectroscopic methods. Gel permeation chromatography (GPC) has been used to establish the molecular weight and molecular weight distribution (polydispersity) of the polymers. A Waters Associates liquid chromatograph equipped with differential refractometer and $10^6$, $10^5$, $10^4$, $10^3$, 500 and 100 Å Ultrastyragel columns was used. Tetrahydrofuran (flow rate of 1.0 mL/min) was used as eluent. The molecular weights are provided as polystyrene equivalents. The terms $M_n$, $M_w$ and $M_w/M_n$ are used to indicate the number and weight average molecular weights and the polydispersity respectively.

Preparation of Di(thiobenzoyl)Disulfide

The title compound was prepared by oxidizing an aqueous solution of dithiobenzoic acid sodium salt with a mild oxidizing agent, e.g. an aqueous solution of iodine.

An aqueous solution of iodine (1.0 N, 100 mL) was added dropwise to a stirred aqueous solution of dithiobenzoic acid sodium salt (0.1 mol in 100 mL of water) at room temperature over 15 minutes. Diethyl ether (100 mL) was added, the organic layer separated and washed twice with water, dried ($Na_2SO_4$), filtered and concentrated in vacuo. Di(thiobenzoyl)disulfide (7.5 g, 50%) was obtained after recrystallization from hot ethanol, m.p. 89–91° C. [lit (Houben, *Chem, Ber.,* 39, 3219–3233, (1906). m.p. 92.5° C.]. $^1$H-nmr (CDCl$_3$) δ (ppm) 7.44 (m, 4H, meta-ArH); 7.62 (m, 2H, para-ArH) and 8.11 (m, 4H, ortho-ArH).

Examples 1 and 4–6 demonstrate the synthesis of a low molecular weight dithio-compound by generating free radicals in the presence of di(thiobenzoyl)disulfide.

Example 1

Preparation of 4-Cyano-4-(thiobenzoylthio) pentanoic Acid

A solution of ethyl acetate (10 mL) containing 4,4'-azobis (4-cyanopentanoic acid) (500 mg) and thiobenzoyl disulfide (612 mg) was placed in a reaction vessel which was degassed by three freeze-evacuate-thaw cycles, sealed under vacuum, and heated at 70° C. for 24 hours. After removal of the volatiles in vacuo, the crude product was subjected to column chromatography (40 g Kieselgel-60, 70–230 mesh) with ethyl acetate:n-hexane:acetonitrile 4:5:1 as eluent, the title compound was obtained as a red oil, 0.51 g (51.2% yield). The product solidified on standing in a freezer at −20° C., m.p. 97–99° C. $^1$H-nmr (CDCl$_3$) δ (ppm) 1.95 (s, 3H, CH$_3$); 2.40–2.80 (m, 4H, CH$_2$CH$_2$); 7.42 (m, 2H, meta-ArH); 7.60 (m, 1H, para-ArH) and 7.91 (m, 2H, ortho-ArH).

The following two examples demonstrate the 'one-pot' synthesis of oligomeric dithio compound and narrow polydispersity polymer by conducting a polymerization in the presence of di(thiobenzoyl)disulfide.

Example 2

Preparation of Low Polydispersity PMMA by Free Radical Initiated Polymerization of Methyl Methacrylate in the Presence of Di(thiobenzoyl) Disulfide A stock solution containing methyl methacrylate (15 mL), azobisisobutyronitrile (20 mg) in benzene (5 mL) was prepared. Aliquots (4 mL) were transferred to ampoules containing di(thiobenzoyl)disulfide (13.8 mg) which were degassed, sealed and heated at 60° C. for the times indicated in the Table. Results are summarized below.

TABLE 1

GPC molecular weight data of PMMA prepared via solution polymerization with thiobenzoyl disulfide at 60° C.

| Entry | Time/hr | Mn$^a$ | Mw/Mn | % Conv. |
|---|---|---|---|---|
| 1 | 16 | 256 | 1.24 | 0.7 |
| 2 | 115.5 | 39666 | 1.10 | 50.4 |

$^a$GPC molecular weight in polystyrene standard equivalents.

Example 3

Preparation of Low Polydispersity Polystyrene by Thermal Polymerization of Styrene in the Presence of Di(thiobenzoyl)Disulfide A stock solution of freshly distilled styrene (5 mL) and di(thiobenzoyl)disulfide (45 mg, 1.47×10$^{-4}$ mol) was prepared. Aliquots (2 mL) of this solution were transferred to ampoules (for entries 2 and 3) and freshly distilled styrene (2 mL) transferred to an ampoule labelled control run (entry 1) which were degassed, sealed and heated at 110° C. for the times indicated in the Table below. The polymerization gave narrow polydispersity polystyrene (PD 1.07) (Table 2, entry 3).

TABLE 2

GPC molecular weight data for the thermal polymerization of styrene with thiobenzoyl disulfide at 100° C.

| Entry | Time/hr | Mn$^a$ | Mw/Mn | % Conv. |
|---|---|---|---|---|
| 1 (control) | 3 | 319638 | 1.62 | 14.8 |
| 2 | 3 | 360 | 1.45 | 2.7 |
| 3 | 16 | 8197 | 1.07 | 30.7 |

$^a$GPC molecular weight in polystyrene standard equivalents.

Example 4

Preparation of 4-Cyano-1-Hydroxylpent-4-yl Dithiobenzoate

The 4-cyano-1-hydroxylpent-4-yl dithiobenzoate was prepared by heating a degassed solution of 4,4'-azobis(4-cyano-n-pentanol) and di(thiobenzoyl)disulfide at 70° C. in ethyl acetate for 24 hours. The desired product was isolated in 46% yield.

Procedure:

A solution of di(thiobenzoyl)disulfide (0.73 g, 2.4 mmol) and 4,4'-azobis(4-cyano-n-pentanol) (0.50 g, 2 mmol) in ethyl acetate (10 mL) was prepared. The mixture was degassed and heated to 70° C. in a Young's vessel for 24 hours. The volatiles were removed under reduced pressure and the residue chromatographed using a mixture of ethyl acetate/petroleum spirits/acetonitrile (6:14:1) as eluant to isolate the title compound (0.49 g, 1.85 mmol, 46%). $^1$H-nmr (CDCl$_3$) δ (ppm) 1.90 (3H, CH$_3$), 2.10 (2H, CH$_2$), 2.30 (2H, CH$_2$), 3.75 (2H, CH$_2$), 7.40, 7.50, 7.90 (5H, ArH).

The following Examples (5–7) demonstrate the use of dithioesters prepared by way of bis(thiobenzoyl)disulfide in the synthesis of narrow polydispersity polymers.

Example 5

Preparation of 2-Cyanobut-2-yl Dithiobenzoate

The 2-cyanobut-2-yl dithiobenzoate was prepared by heating a degassed solution of 2,2'-azobis(2-cyano-2-butane) and di(thiobenzoyl)disulfide at 70° C. in ethyl acetate for 24 hours. The desired product was isolated in 82% yield.

Procedure:

A solution of di(thiobenzoyl)disulfide (0.4 g, 1.3 mmol) and 2,2'-azobis(2-cyano-2-butane) (0.53 g, 2.76 mmol) in ethyl acetate (5 mL) was prepared. The mixture was degassed and heated at 70° C. in a Young's vessel for 24 hours. The volatiles were removed under reduced pressure and the residue chromatographed on a silica-gel column using a mixture of ethyl acetate/n-hexane (1:9) as eluent to isolate the title compound (0.25 g, 82%). $^1$H-nmr (CDCl$_3$) δ (ppm) 1.23 (t, 3H), 1.92 (s, 3H), 2.10 (dt, 1H), 2.30 (dt, 1H), 7.40 (m, 2H, meta-ArH), 7.57 (m, 1H, para-ArH) and 7.91 (m, 2H, ortho-ArH).

Example 6

Preparation of 1-Cyano-1-Cyclohexyl Dithiobenzoate

Similarly, as in Example 5, the 1-cyano-1-cyclohexyl dithiobenzoate was prepared by heating a degassed solution of 1,1'-azobis(cyclohexanecarbonitrile) and di(thiobenzoyl) disulfide at 70° C. in ethyl acetate for 48 hours.

Procedure:

A solution of di(thiobenzoyl)disulfide (0.4 g, 1.3 mmol) and 1,1'-azobis(cyclohexanecarbonitrile) (0.67 g, 2.74 mmol) in ethyl acetate (5.0 mL) was prepared. The mixture was degassed and heated at 70° C. in a Young's vessel for 48 hours. The volatiles were removed under reduced pressure and the residue chromatographed on a silica-gel column using a mixture of ethyl acetate/petroleum spirits 40–60° C. (1:9) as eluent to isolate the title compound.

Example 7

Preparation of Low Polydispersity Polystyrene in the Presence of Hydroxy-Terminated Dithioester, 4-Cyano-1-Hydroxypent-4-yl Dithiobenzoate A solution of hydroxy-terminated dithioester such as 4-cyano-1-hydroxylpent-4-yl dithiobenzoate (31.3 mg) in styrene (2 mL) was prepared and transferred to an ampoule. The contents were degassed and heated at 100° C. for 16 hrs. The volatiles were removed and the residue dried to constant weight and analysed by GPC (see Table 3).

TABLE 3

GPC molecular weight data of polymerisation of styrene with 4-cyano-1-hydroxylpent-4-yl dithiobenzoate at 100° C..

| Dithioester | Time/hr | Mn[a] | Mw/Mn | % Conv. |
|---|---|---|---|---|
| Hydroxy dithio | 16 | 2808 | 1.04 | 17.0 |

[a]GPC molecular weight in polystyrene standard equivalents.

The end groups in polystyrene, prepared in the presence of the hydroxy-terminated dithioester were confirmed by the $^1$H-nmr spectroscopy. The signals at δ 3.4–3.5 ppm were assigned to the $CH_2OH$ protons and those at δ 7.9 ppm to the ortho-phenyl protons of the terminal thiobenzoylthio group.

Example 8

Preparation of Low Polydispersity Poly(Methyl Methacrylate) in the Presence of Hydroxy-Terminated Dithioester, 4-Cyano-1-Hydroxypent-4-yl Dithiobenzoate A stock solution of MMA (7.5 mL), benzene (2.5 mL) and AIBN (10 mg) was prepared and labelled Solution (I). A 2 mL aliquot of solution (I) was used as the control, labelled A. An aliquot of solution (I) (4 mL) was used to dissolve 12 mg of 4-cyano-1-hydroxylpent-4-yl dithiobenzoate, divided into two portions and labelled B and C. The samples were degassed, the ampoules sealed under vacuum and heated at 60° C. for period of times indicated in Table 4. The volatiles in each sample were removed, the residue dried to constant weight and the products analysed by GPC. The results are summarized in Table.

TABLE 4

GPC molecular weight data of polymerization of MMA with 4-cyano-1-hydroxylpentyl dithiobenzoate using AIBN as initiator at 60° C..

| Entry | Time/hr | Mn[a] | Mw/Mn | % Conv. |
|---|---|---|---|---|
| 1 (control) | 3 | 310 080 | 1.64 | 76.0 |
| 2 | 3 | 11 200 | 1.14 | 17.0 |
| 3 | 16 | 55 300 | 1.05 | 92.0 |

[a]GPC molecular weight in polystyrene standard equivalents.

Example 9

Preparation of Low Polydispersity Poly(N,N-dimethylaminoethyl Methacrylate) in the Presence of Carboxy-Terminated Dithioester, 4-Cyano-4-(Thiobenzoyl)Pentanoic Acid A stock solution comprising of N,N-dimethylaminoethyl methacrylate monomer (DMAEMA) (7.5 mL), 4,4'-azobis (4-cyanopentanoic acid) (8.5 mg) and 4-cyano-4-(thiobenzoylthio)pentanoic acid (35.0 mg) in ethyl acetate (10 mL) was prepared. Aliquots of the stock solution (4 mL) were transferred to three ampoules which were degassed, sealed, and heated at 60° C. for the specified times listed in Table. The polymerizations show excellent control in molecular weight and polydispersity (1.1–1.3).

TABLE 5

Molecular weight data of poly(DMAEMA) using Carboxy-terminated dithioester, 4-cyano-4-(thiobenzoylthio)pentanoic acid at 60° C..

| Entry | Time/hr | Mn[a] | Mw/Mn | % Conv. |
|---|---|---|---|---|
| 1 | 4 | 3316 | 1.31 | 9.0 |
| 2 | 8 | 11257 | 1.12 | 28.3 |
| 3 | 16 | 21559 | 1.13 | 61.8 |

[a]GPC molecular weight in polystyrene equivalents.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A process for the synthesis of a dithioester of formula I:

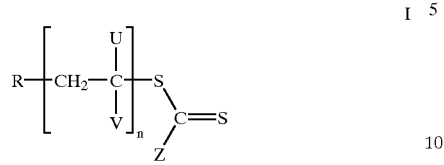

where R is derived from a free radical R. and is selected from the group consisting of optionally substituted alkyl; optionally substituted, saturated, unsaturated or aromatic carbocyclic rings; optionally substituted, saturated, unsaturated or aromatic heterocyclic rings; optionally substituted alkylthio, optionally substituted arylthio; optionally substituted alkoxy, optionally substituted dialkylamino; organometallic species; and polymer chains; R. is a free radical leaving group;

U is independently selected from the group consisting of hydrogen; halogen; and $C_{1-4}$ alkyl optionally substituted with one or more substituents independently selected from the group consisting of hydroxy, carboxy, acyloxy, OR", $O_2CR"$ and $CO_2R"$;

V is independently selected from the group consisting of hydrogen, halogen, R", $CO_2H$, $CO_2R"$, COR", CN, $CONH_2$, CONHR", $CONR_2"$, $O_2CR"$ and OR";

Z is selected from the group consisting of hydrogen, chlorine, optionally substituted alkyl, optionally substituted aryl, optionally substituted alkylthio, optionally substituted alkoxycarbonyl, —$CO_2R"$, —$CO_2H$, —$O_2CR"$, —$CONR_2"$, cyano, [—P(=O)(OR"$_2$)], and [—P(=O)R"$_2$];

R" is independently selected from the group consisting of optionally substituted $C_{1-18}$ alkyl, optionally substituted $C_{2-18}$ alkenyl, optionally substituted aryl, optionally substituted heterocyclyl, optionally substituted aralkyl, optionally substituted alkaryl, wherein said acyl, acyloxy, carboxy (and salts), sulphonic acid (and salts), alkoxycarbonyl, aryloxycarbonyl, isocyanato, cyano, silyl, halo and dialkylamino;

and n is 0 or a positive integer, which process includes contacting a disulphide of the Formula II:

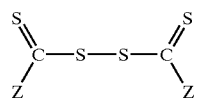

with
(i) in the case of n=0, a free radical of the formula R., or
(ii) in the case of n>0, a free radical of the formula R. and at least one monomer of the formula III

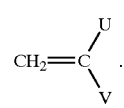

2. A process for the synthesis of a dithioester of Formula I as defined in claim 1 from a compound of formula V

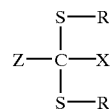

where Z is as defined above,

X is hydrogen, halogen, acyl, aryl or phosphine oxide, and each R is the same or different and is selected from the group consisting of optionally substituted alkyl; optionally substituted, saturated, unsaturated or aromatic carbocyclic rings; optionally substituted, saturated, unsaturated or aromatic heterocyclic rings; optionally substituted alkylthio, optionally substituted arylthio; optionally substituted alkoxy; optionally substituted dialkylamino; organometallic species; and polymer chains; and where the corresponding radical, R., is a free radical leaving group; by A) in the case of n=0,
   (i) where X is not hydrogen, homolytic cleavage of the C—X bond of a compound of formula V and subsequent elimination of R.,
   (ii) where X is hydrogen, contacting a compound of formula V with a hydrogen abstracting radical followed by elimination of R., or
   (iii) contacting a compound of formula V with a Lewis acid followed by elimination of R., or B) in the case of n>0,
   performing any of (i), (ii) or (iii) in the presence of a monomer of formula III as defined in claim 1.

3. A process for the synthesis of a composition of matter of Formula I as defined in claim 1 including contacting a compound of formula VI

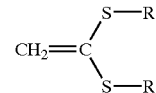

where each R is the same or different and is selected from the group consisting of optionally substituted alkyl; optionally substituted, saturated, unsaturated or aromatic carbocyclic rings; optionally substituted, saturated, unsaturated or aromatic heterocyclic rings; optionally substituted alkylthio, optionally substituted arylthio; optionally substituted alkoxy; optionally substituted dialkylamino; organometallic species; and polymer chains; and where the corresponding radial R., is a free radical leaving group;

with (i) in the case of n=0,
a free radical of formula R., or
(ii) in the case of n>0,
a free radical of formula R. and
a monomer of Formula III.

4. A process according to claim 1 wherein R. is capable of initiating free radical polymerisation.

5. A process according to claim 1 wherein R is a polymer chain.

6. A process according to claim 5 wherein the polymer chain is produced by means of free radical polymerisation.

7. A process according to claim 5 wherein the polymer chain includes or consists of a polymer produced by non-free radical means.

8. A process according to claim 7 wherein the polymer produced by non-free radical means is a condensation polymer.

9. A process according to claim 1 wherein R is derived from a dithioester of Formula I generated in situ.

10. A process according to claim 1 wherein R is derived from an initiating radical.

11. A process according to claim 1 wherein R is derived from a propagating radical.

12. A process according to claim 1 wherein the monomer of Formula III is selected from:
methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethylacrylamide, N-n-butylmethylacrylamide, N-methylolmethylacrylamide, N-ethylolmethacrylamide, N-tert-butylacrylamide, N-n-butylacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), n-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethyl-silylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, isoprene, chloroprene, ethylene and propylene.

13. A process according to claim 12 wherein the monomer is selected from styrenic monomers and methacrylate monomers.

14. A process according to claim 2 wherein Z is a group capable of activating the C=S bond of the dithioester of Formula I towards radical addition, while not substantially slowing the rate of fragmentation.

15. A process according to claim 3 where the group $RCH_2$ is selected from a group capable of activating the C=S bond of the dithioester of Formula I towards radical addition, while not substantially slowing the rate of fragmentation.

16. A process according to claim 10 wherein the initiating radical is derived from a compound selected from the group consisting of:
2,2'-azobis(isobutyronitrile), 2,2'-azobis(2-cyano-2-butane), dimethyl 2,2'-azobis(methyl isobutyrate), 4,4'-azobis(4-cyanopentanoic acid), 4,4'-azobis(4-cyanopentan-1-ol), 1,1'-azobis(cyclohexanecarbonitrile), 2-(t-butylazo)-2-cyanopropane, 2,2'-azobis[2-methyl-(N)-(1,1)-bis(hydroxymethyl)-2-hydroxyethyl] propionamide, 2,2'-azobis[2-methyl-N-hydroxyethyl)]-propionamide, 2,2'-azobis(N,N'-dimethyleneisobutyramidine) dihydrochloride, 2,2'-azobis(2-amidinopropane) dihydrochloride, 2,2'-azobis(N,N'-dimethyleneisobutyramine), 2,2'-azobis(2-methyl-N-[1,1-bis(hydroxymethyl)-2-hydroxyethyl] propionamide), 2,2'-azobis(2-methyl-N-[1,1-bis(hydroxymethyl)ethyl]propionamide), 2,2'-azobis[2-methyl-N-(2-hydroxyethyl)propionamide], 2,2'-azobis(isobutyramide)dihydrate, 2,2'-azobis(2,2,4-trimethylpentane), 2,2'-azobis(2-methylpropane), dilauroyl peroxide, tertiary amyl peroxides and tertiary amyl peroxydicarbonates.

17. A process according to claim 11 wherein the propagating radical is formed by addition of an initiator to the monomer.

18. A process according to claim 17 wherein the initiator is selected from:
t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, potassium peroxydisulfate, ammonium peroxydisulfate, di-t-butyl hyponitrite, dicumyl hyponitrite.

19. A process for preparing a homopolymer of Formula I as claimed in claim 1 wherein a single monomer of Formula III is contacted with the disulphide of Formula II and free radical of the formula R.

20. A process for preparing a copolymer of Formula I as claimed in claim 1 wherein more than one monomer of Formula III is contacted with the disulphide of Formula II and free radical of the formula R.

21. A process for preparing a block copolymer of Formula I as claimed in claim 1 wherein a first monomer of Formula III is contacted with the disulphide of Formula II and free radical of formula R. to produce a homopolymer of Formula I, said homopolymer being contacted with a second monomer of Formula III and a free radical of formula R.

22. A process of claim 3 wherein the compound of Formula V is a thioacetal of benzoin.

23. A polymer prepared in accordance with claim.

24. A process according to claim 1 wherein R. is capable of initiating free radical polymerisation.

25. A process according to claim 1 wherein n>0.

* * * * *